(12) United States Patent
Bordeaux (10) Patent No.: US 11,596,521 B2
(45) Date of Patent: Mar. 7, 2023

(54) INTERVERTEBRAL IMPLANT FOR QUADRUPEDS

(71) Applicant: DePuy Synthes Products, Inc., Raynham, MA (US)

(72) Inventor: Jean-Noel Bordeaux, West Chester, PA (US)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 16/502,954

(22) Filed: Jul. 3, 2019

(65) Prior Publication Data

US 2021/0000607 A1 Jan. 7, 2021

(51) Int. Cl.
*A61F 2/44* (2006.01)
*A61F 2/30* (2006.01)

(52) U.S. Cl.
CPC .......... *A61F 2/442* (2013.01); *A61F 2/30749* (2013.01); *A61F 2/30771* (2013.01); *A61F 2002/307* (2013.01); *A61F 2002/3093* (2013.01); *A61F 2002/30507* (2013.01); *A61F 2002/30904* (2013.01); *A61F 2310/00131* (2013.01)

(58) Field of Classification Search
CPC ............ A61B 17/00; A61B 17/80; A61F 2/44
See application file for complete search history.

(56) References Cited

U.S. PATENT DOCUMENTS

| | | | | |
|---|---|---|---|---|
| 6,228,085 | B1* | 5/2001 | Theken | A61B 17/7059 606/289 |
| 6,342,055 | B1* | 1/2002 | Eisermann | A61B 17/8886 623/17.16 |
| 9,241,810 | B1* | 1/2016 | Rumi | A61F 2/447 |
| 9,351,845 | B1 | 5/2016 | Pimenta et al. | |
| 2004/0122518 | A1* | 6/2004 | Rhoda | A61F 2/4465 623/17.11 |
| 2006/0241760 | A1* | 10/2006 | Randall | A61F 2/447 623/17.11 |
| 2010/0168798 | A1* | 7/2010 | Clineff | A61F 2/4611 606/279 |
| 2011/0230971 | A1 | 9/2011 | Donner et al. | |
| 2015/0142115 | A1* | 5/2015 | Richerme | A61F 2/442 623/17.16 |

FOREIGN PATENT DOCUMENTS

| | | |
|---|---|---|
| FR | 2795945 A1 | 1/2001 |
| WO | 2005/097004 A2 | 10/2005 |
| WO | 2007/098288 A2 | 8/2007 |
| WO | 2014/005154 A1 | 1/2014 |

* cited by examiner

Primary Examiner — Matthew J Lawson
(74) Attorney, Agent, or Firm — BakerHostetler (57) ABSTRACT

A low profile intervertebral implant for implantation in an intervertebral disc space between adjacent vertebral bodies of a quadruped. The intervertebral implant includes a plate and a spacer that extends from the plate. The intervertebral implant can define geometries that nest with complementary geometries of the vertebral bodies. Further, the plate can include fixation holes that extend along trajectories such that screws inserted through the fixation holes and driven into the respective vertebral bodies can purchase with dense cortical bone.

19 Claims, 6 Drawing Sheets

INTERVERTEBRAL IMPLANT FOR QUADRUPEDS

BACKGROUND

Cervical spondylomyelopathy (CSM), also known as wobbler disease, affects primarily large and giant-breed canines, such as dobermans, great danes, and the like. Wobbler disease can cause an unsteady gait and weakness in canines. CSM can be caused by many different conditions, including malformation of the vertebrae, intervertebral disc protrusion, stenosis of the vertebral canal, and disease of the interspinal ligaments, ligamenta flava, and articular facets of the vertebrae. The instability can result in compression of the spinal cord.

Surgical interbody fusion is often performed to fuse adjacent vertebrae to each other, thereby eliminating the spinal cord compression. Conventional surgical techniques include distraction of the vertebral bodies, spanning the disc space with an intervertebral spacer, typically made from polymethylmethacrylate (PMMA), and fixing the spacer in the disc space using screws or pins or the like. However, current surgical techniques risk complications, such as backing out of the screws or pins, cracking of the spacer, laceration of vertebral arteries, spinal nerves, nerve roots, and trauma to the spinal cord. Complications can further include improper placement of the pins or screws which are intended be bicortical, meaning that they are intended to thread into both a near cortex and a far cortex of the vertebral body.

What is therefore needed is an improved system for providing intervertebral fixation of a quadruped, and in particular of a canine.

SUMMARY

In one example, an intervertebral implant is configured to be implanted in an intervertebral disc space of a quadruped, the intervertebral disc space defined by a cranial vertebral body and a caudal vertebral body. The implant can include a plate that defines a ventral plate end and a dorsal plate end spaced opposite the ventral plate end in a dorsal direction. The plate can further include a plurality of fixation apertures that extend through the plate from the ventral plate end to the dorsal plate end. The implant can further include a spacer that extends in the dorsal direction from the plate. The spacer can define a caudal surface and a cranial surface opposite the caudal surface in a cranial direction. The caudal and cranial surfaces can be configured to grip the caudal and cranial vertebral bodies, respectively. The cranial surface can be convex in a first plane that is oriented along the dorsal direction and the cranial direction, and the cranial surface is convex in a second plane that is oriented along the cranial direction and a lateral direction that is substantially perpendicular to each of the dorsal direction and the cranial direction. The caudal surface can be substantially straight and liner in the first plane, and the caudal surface can be convex in the second plane.

BRIEF DESCRIPTION OF THE DRAWINGS

The foregoing summary, as well as the following detailed description of the preferred embodiments of the application, will be better understood when read in conjunction with the appended drawings. For the purposes of illustrating the preferred intervertebral implants of the present application, there is shown in the drawings preferred embodiments. It should be understood, however, that the application is not limited to the precise arrangements and instrumentalities shown. In the drawings.

DETAILED DESCRIPTION

The present disclosure can be understood more readily by reference to the following detailed description taken in connection with the accompanying figures and examples, which form a part of this disclosure. It is to be understood that this disclosure is not limited to the specific devices, methods, applications, conditions or parameters described and/or shown herein, and that the terminology used herein is for the purpose of describing particular embodiments by way of example only and is not intended to be limiting of the scope of the present disclosure. Also, as used herein, the singular forms "a," "an," and "the" include "at least one" and a plurality, unless otherwise indicated. Further, reference to a plurality as used herein includes the singular "a," "an," "one," and "the," and further includes "at least one" unless otherwise indicated. Further still, the term "at least one" can include the singular "a," "an," and "the," and further can include a plurality, unless otherwise indicated. Further yet, reference to a particular numerical value in the specification including the appended claims includes at least that particular value, unless otherwise indicated.

The term "plurality", as used herein, means more than one, such as two or more. When a range of values is expressed, another example includes from the one particular value and/or to the other particular value. The words "substantially" and "approximately" as used herein with respect to a shape, size, or other parameter or numerical value includes the stated shape, size, or other parameter or numerical value, and further includes plus and minus 10% of the stated shape, size, or other parameter or numerical value.

Figure 1A:
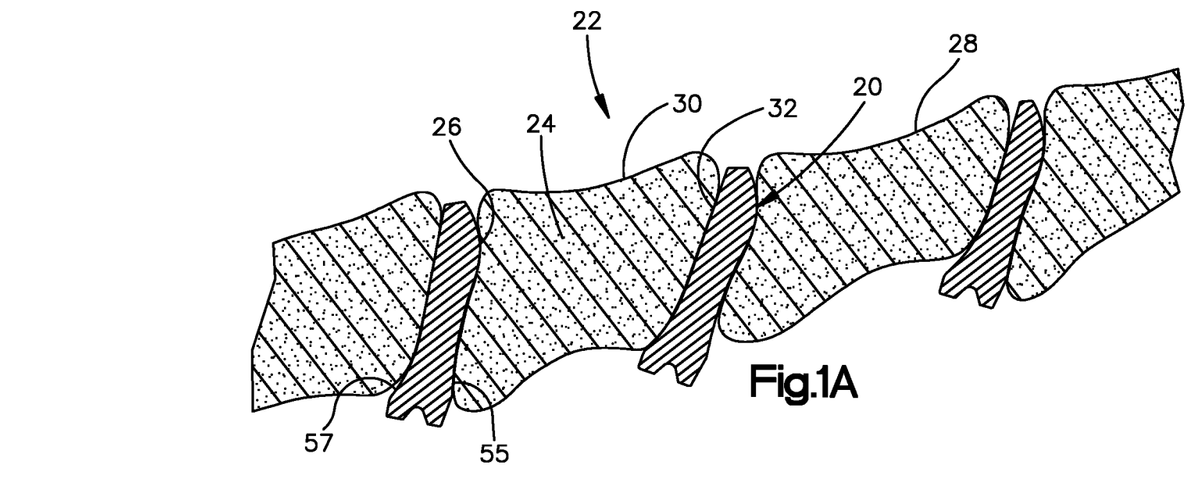
FIG. 1A is a cross-sectional view showing a portion of a spinal column of a canine, and an intervertebral implant that has been implanted in an intervertebral space between adjacent vertebrae.
Figure 1B:
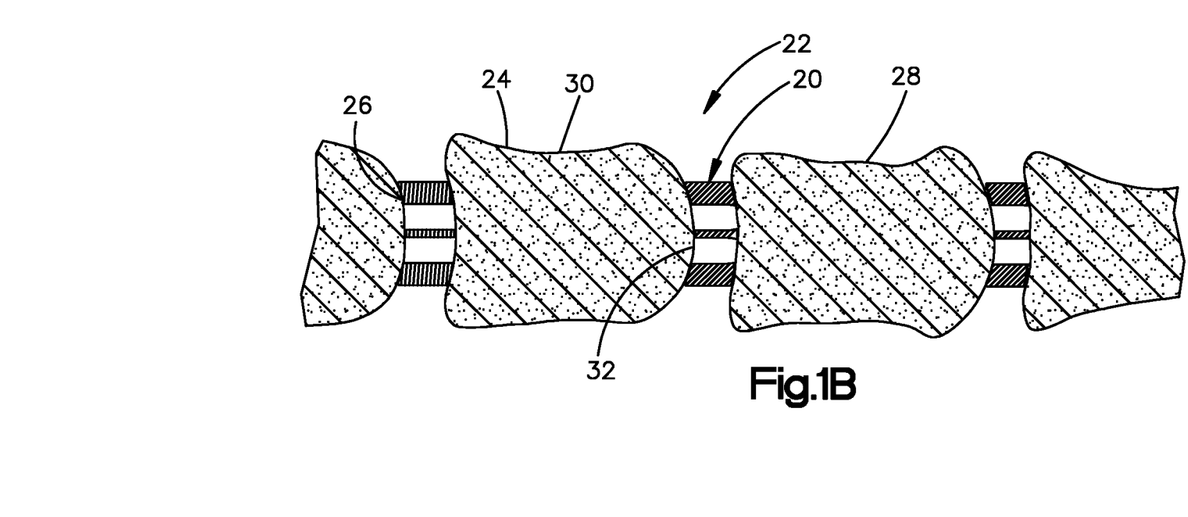
FIG. 1B is another cross-sectional view of the portion of the spinal column illustrated in FIG. 1A.

Referring initially to FIGS. 1A-1B, an intervertebral implant 20 is configured to be implanted into the spine 22 of a quadruped, which can be a canine. The spine 22 of the quadruped includes a plurality of vertebrae 24 separated from each other by an intervertebral disc space 26 that contains disc material in a healthy quadruped. The vertebrae 24 include a first or cranial vertebral body 28 and an adjacent second or caudal vertebral body 30 separated from the cranial vertebral body 28 by a respective intervertebral disc space 32. When the quadruped suffers from a condition that indicates fusion of the adjacent vertebral bodies 28 and 30, the intervertebral implant 20 can be implanted into the disc space 32 that fuses the vertebral bodies 28 and 30 to each other following a discectomy procedure whereby some or all of the disc material is removed from the disc space 32. In one example, the quadruped can be suffering from CSM, and thus the vertebral bodies 28 and 30 can be cervical vertebral bodies. While the intervertebral implant 20 can contain features that are designed for implantation in the cervical region of the spine as described below, it should be appreciated that the vertebral bodies 28 and 30 can alternatively be located in the thoracic or lumbar regions of the quadruped.

Figure 2A:
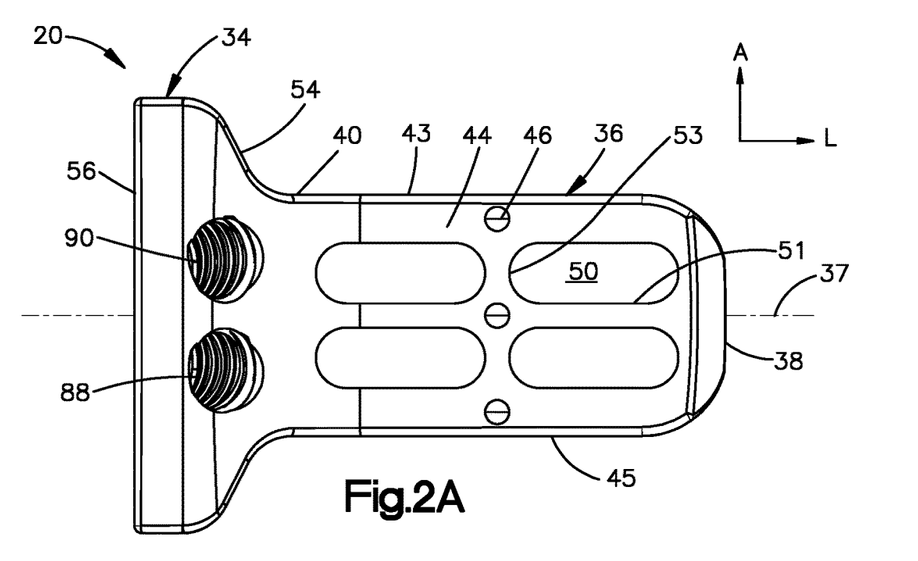
FIG. 2A is a plan view of the intervertebral implant illustrated in FIG. 1A, showing a plate and a spacer.
Figure 2B:
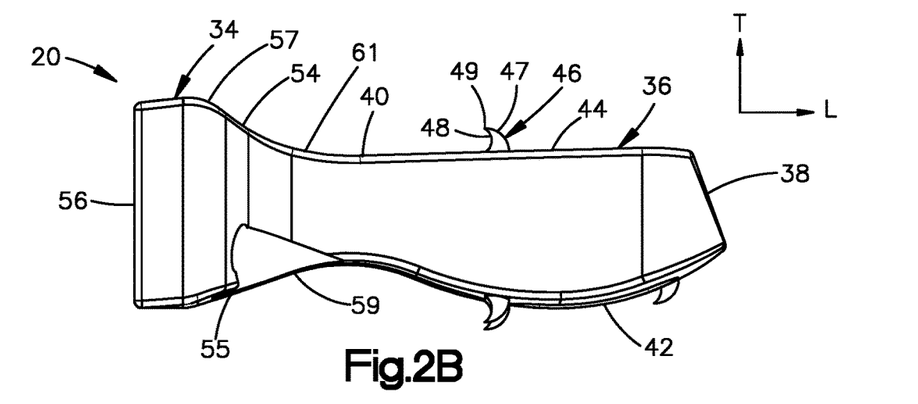
FIG. 2B is a side elevation view of the intervertebral implant illustrated in FIG. 2A.

Referring also to FIGS. 2A-2B, the implant 20 can include a plate 34 and a spacer 36 that extends from the plate 34. The spacer 36 is preferably configured and dimensioned for implantation into the intervertebral disc space 32 between the first and second vertebral bodies 28 and 30. The spacer 36 is preferably sized and configured to maintain and/or restore a desired intervertebral disc height between the adjacent vertebral bodies 28 and 30. The plate 34 can be configured to be fixed to the first and second vertebral bodies 28 and 30.

The intervertebral implant 20 may be constructed of any suitable material or combination of materials including, but not limited to polymer (e.g. PEEK), titanium, titanium alloy, stainless steel, Nitinol, tantalum nitride (TaN), allograft bone, bioresorbable material, magnesium, composites, synthetic bone-welding polymers, etc. The plate 34 may be formed of a different material than the spacer 36. For example, the plate 34 may be formed of a metallic material such as, for example, a titanium or a titanium alloy, and the spacer 36 may be formed of a non-metallic material such as, for example, an allograft, a polymer, a bioresorbable material, a ceramic, etc. Alternatively, the plate 34 and the spacer 36 may be formed from the same material. For example, the plate 34 and the spacer 36 may both be constructed of tantalum nitride (TaN) or any suitable alternative material as desired.

The spacer 36 may include a first or leading end 38 with respect to insertion into the disc space 32, and a second or trailing end 40 that is opposite the leading end 38 along a longitudinal direction L. A forward or insertion direction into the disc space 32 can thus refer to a direction from the trailing end 40 toward the leading end 38. A rearward direction opposite the forward direction can refer to a direction from the leading end 38 toward the trailing end 40. The intervertebral implant 20 can be configured such that the insertion direction is oriented along any suitable approach as desired, including but not limited to a lateral approach. Thus, the leading end 38 can be referred to as a dorsal end, and the trailing end 40 can be referred to as a ventral end. Further, the forward or insertion direction can be referred to as a dorsal direction, and vice versa. The rearward direction can be referred to as a ventral direction, and vice versa. The ventral direction is opposite the dorsal direction. Accordingly, the term "longitudinal direction L" can be used interchangeably with a dorsal-ventral direction that either or both of the dorsal direction and the ventral direction, and vice versa. A ventral-dorsal direction includes each of the dorsal direction and the ventral direction.

The spacer 36 can extend along a central spacer axis 37. The central spacer axis 37 can be oriented along the longitudinal direction L, and can bifurcate the spacer 36 into two substantially equally sized and shaped halves. The spacer 36 can include a first or cranial wall that defines an outer first or cranial surface 42. The outer cranial surface 42 is configured to face the cranial direction when implanted. The spacer 36 can include a second or caudal wall that defines an outer second or caudal surface 44. The outer caudal surface 44 is configured to face the caudal direction when implanted. Thus, the caudal surface 44 can face opposite the cranial surface 42 along a transverse direction T that is substantially perpendicular to the longitudinal direction L. The caudal surface 44 can further be said to be opposite the cranial surface 42 in a caudal direction. Similarly, the cranial surface 42 can further be said to be opposite the caudal surface 44 in a cranial direction Thus, the term "transverse direction T" can be used interchangeably with either or both of the cranial direction and the caudal direction, and vice versa. A caudal-cranial direction includes each of the caudal direction and the cranial direction.

The spacer 36 can further include first and second opposed lateral walls 43 and 45 that are opposite each other along a lateral direction A that is substantially perpendicular to each of the transverse direction T and the longitudinal direction L. The spacer can define a midplane 39 (see FIGS. 5B-5C) that is oriented along the longitudinal direction L and the transverse direction T, and includes the central spacer axis 37. The midplane 39 can thus divide the spacer 36 into equal lateral halves. The midplane 39 can further divide the plate 34 into equal lateral halves. Further, the implant 20 can be substantially symmetrical about the midplane 39.

With continuing reference to FIGS. 2A-2B, the cranial surface 42 can be configured to face the cranial vertebral body 28, and the caudal surface 44 can be configured to face the caudal vertebral body 30 when the spacer 36 is disposed in the disc space 32. Further, the cranial surface 42 can be configured to abut the cranial vertebral body 28, and the caudal surface 44 can be configured to abut the caudal vertebral body 30 when the spacer 36 is disposed in the disc space 32.

In one example, the cranial surface 42 can be configured to grip the cranial vertebral body 28, and the caudal surface 44 can be configured to grip the caudal vertebral body 30 when the spacer 36 is disposed in the disc space 32. The intervertebral implant 20 can include a plurality of teeth 46 that project out from the cranial and caudal surfaces 42 and 44, respectively. The teeth 46 are configured to penetrate the vertebral endplates of the respective cranial and caudal vertebral bodies 28 and 30. Thus, the intervertebral implant 20 can be configured to resist migration within the disc space 32 after implantation. The teeth 46 can be configured in any suitable manner as desired. In particular, the teeth 46 can include a leading surface 47 with respect to the insertion direction, and a trailing surface 48 opposite the leading surface 47. The leading surface 47 can be convex, and the trailing surface 48 can be concave. The leading and trailing surfaces 47 and 48 can converge to a sharp pointed tip 49. Distal ends of the leading and trailing surfaces 47 and 48 can extend along the rearward direction as they converge to the tip 49.

Alternatively or additionally, the spacer 36 can include one or more windows 50 that are designed to receive bone graft material. The bone graft material can further fuse the intervertebral implant 20 to the first and second vertebral bodies 28 and 30. The windows 50 can extend from the cranial surface 42 to the caudal surface 44. The windows 50 can be configured to receive bone graft material so as to promote bone growth through the windows 50 following implantation of the intervertebral implant 20 into the disc space 32. Alternatively or in addition, the spacer 36 may have one or more lateral channels extending through the spacer 20 from either or both of the lateral walls 45 for receiving bone graft material. The lateral channels can be open to the windows 50 in some examples. The spacer 36 can include a plurality of longitudinally oriented ribs 51 and laterally oriented ribs 53 that separate and define the windows 50. The teeth 46 can extend out from the ribs 51 and 53.

The spacer 36 can be shaped to substantially match the geometry of the vertebral endplates of the first and second vertebral bodies 28 and 30. In one example shown in FIG. 2B, at least a portion up to an entirety of the cranial surface 42 can be curved as it extends in the insertion direction. For instance, a least a portion up to an entirety of the cranial surface 42 can be curved as it extends from the plate 34 to the leading end 38. In particular, at least a portion up to an entirety of the cranial surface 42 can be convex as it extends from the plate 34 to the leading end 38. Thus, the cranial surface 42 can be curved in a first plane that is oriented along the longitudinal direction L and the transverse direction T. For instance, the cranial surface 42 can be convex in the first plane that is oriented along the longitudinal direction L and the transverse direction T. The cranial surface 42 can be defined by a first radius of curvature in the first plane that can range from approximately 5 mm to approximately 20 mm. For instance, the first radius of curvature can range from approximately 10 mm to approximately 15 mm. In one example, the first radius of curvature can be approximately 11 mm. In another example, the first radius of curvature can be approximately 15 mm. Further, the first radius of curvature can be constant or variable along the length of the cranial surface 42 in the first plane. Thus, a first portion of the cranial surface 42 can be defined by a radius of curvature of approximately 11 mm, and a second portion of the cranial surface 42 can be defined by a radius of curvature of approximately 15 mm. In one example, the cranial surface 42 can be convex in all first planes oriented along the longitudinal direction L and the transverse direction T and arranged from the first lateral wall 43 to the second lateral wall 45.

With continuing reference to FIG. 2B, at least a portion up to an entirety of the caudal surface 44 can be substantially straight and linear as it extends in the insertion direction. For instance, a least a portion up to an entirety of the caudal surface 44 can be substantially straight and linear as it extends from the plate 34 to the leading end 38. For instance, at least a portion up to an entirety of the caudal surface 44 can be substantially straight and linear as it extends from the plate 34 to the leading end 38. Thus, the caudal surface 44 can be straight and linear in the first plane that is oriented along the longitudinal direction L and the transverse direction T. In one example, the caudal surface 44 can be substantially straight and linear in all first planes oriented along the longitudinal direction L and the transverse direction T and arranged from the first lateral wall 43 to the second lateral wall 45.

Figure 2C:
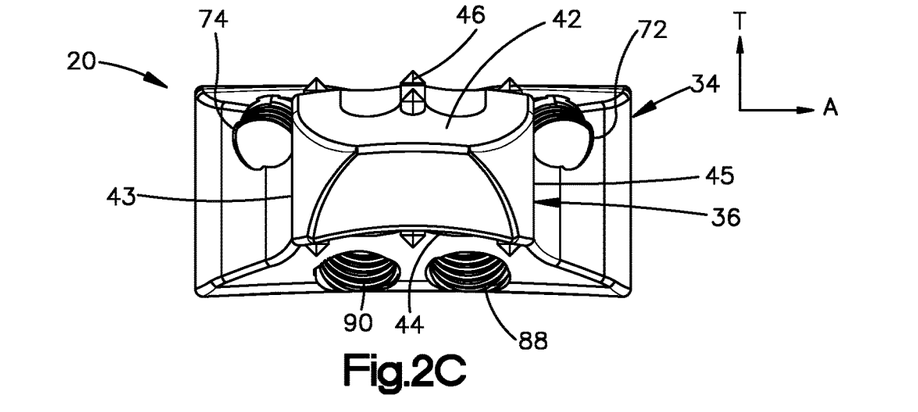
FIG. 2C is an end elevation view of the intervertebral implant illustrated in FIG. 2A.

Further, as shown in FIG. 2C, each of the cranial and caudal surfaces 42 and 44 can be curved in a plane that is oriented along the transverse direction T and the lateral direction A. In particular, at least a portion up to an entirety of the cranial surface 42 can be curved as it extends along the lateral direction A. For instance, a least a portion up to an entirety of the cranial surface can be curved as it extends from the first lateral wall 43 to the second lateral wall 45. In particular, at least a portion up to an entirety of the cranial surface 42 can be convex as it extends from the first lateral wall 43 to the second lateral wall 45. Thus, the cranial surface 42 can be curved in a second plane that is oriented along the lateral direction A and the transverse direction T. For instance, the cranial surface 42 can be convex in the second plane that is oriented along the lateral direction A and the transverse direction T. The cranial surface 42 can be defined by a second radius of curvature in the second plane that ranges from approximately 10 mm to approximately 25 mm. For instance, the second radius of curvature can range from approximately 15 mm to approximately 20 mm. In one example, the second radius of curvature can be approximately 17 mm. Further, the second radius of curvature can be constant or variable along the length of the cranial surface 42 in the second plane. Thus, the radius of curvature of the cranial surface 42 in the second plane can be greater than the first radius of curvature of the cranial surface 42 in the first plane. In one example, the cranial surface 42 can be convex in all second planes oriented along the lateral direction A and the transverse direction T and arranged from the first lateral wall 43 to the second lateral wall 45. Thus, the cranial surface 42 can be geometrically configured to match a complementary geometry of the vertebral endplate of the cranial vertebral body 28.

Similarly, with continuing reference to FIG. 2C, at least a portion up to an entirety of the caudal surface 44 can be curved as it extends along the lateral direction A. For instance, a least a portion up to an entirety of the caudal surface 44 can be curved as it extends from the first lateral wall 43 to the second lateral wall 45. In particular, at least a portion up to an entirety of the caudal surface 44 can be concave as it extends from the first lateral wall 43 to the second lateral wall 45. Thus, the caudal surface 44 can be curved in the second plane that is oriented along the lateral direction A and the transverse direction T. For instance, the caudal surface 44 can be concave in the second plane that is oriented along the lateral direction A and the transverse direction T. The caudal surface 44 can be defined by a radius of curvature in the second plane that ranges from approximately 5 mm to approximately 25 mm. For instance, the radius of curvature of the caudal surface 44 in the second plane can range from approximately 10 mm to approximately 20 mm. In one example, the radius of curvature of the caudal surface 44 in the second plane can be approximately 15 mm. Thus, the radius of curvature of the caudal surface 44 in the second plane can be less than the second radius of curvature of the cranial surface 42 in the second plane. In one example, the cranial surface 42 can be concave in all second planes oriented along the lateral direction A and the transverse direction T and arranged from the first lateral wall 43 to the second lateral wall 45. Thus, the caudal surface 44 can be geometrically configured to match a complementary geometry of the vertebral endplate of the caudal vertebral body 30. In one example, the cranial surface 42 and the caudal surface 44 can extend substantially parallel to each other in the second plane. While specific geometries of the cranial and caudal surfaces 42 and 44 have been described in one example, the geometries can vary as desired.

Figure 3:
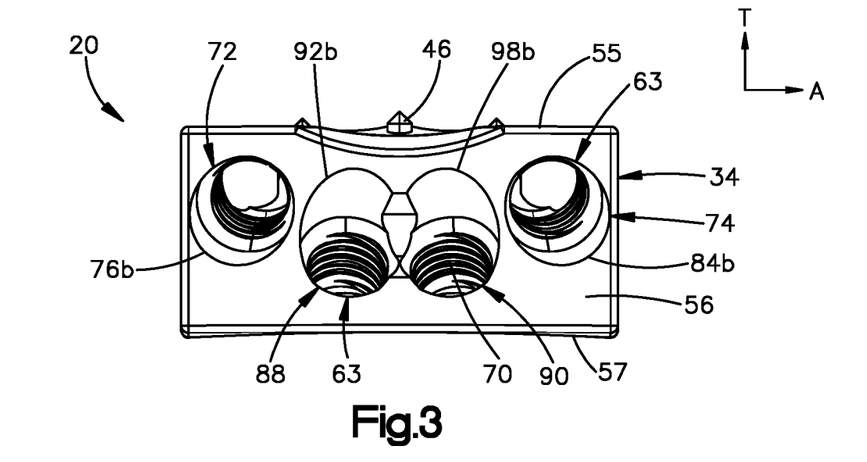
FIG. 3 is another end elevation view of the intervertebral implant illustrated in FIG. 2A.
Figure 4:
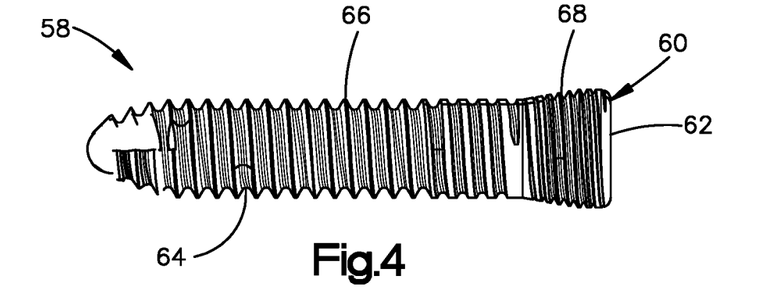
FIG. 4 is a side elevation view of a bone screw among a plurality of bone screws configured to fix the intervertebral implant illustrated in FIG. 2A to the adjacent vertebrae of FIG. 1A.

Referring now to FIGS. 2A-3, the plate 34 can be monolithic with the spacer 36. Alternatively, the plate 34 can be separate from and attached to the spacer 36. The plate 34 can extend out with respect to both the first lateral wall 43 and the second lateral wall 45 of the spacer 36 along the lateral direction A. Further, the plate 34 can extend out with respect to the cranial surface 42 of the spacer 36 a first distance in the cranial direction. Further still, the plate 34 can extend out with respect to the caudal surface 44 of the spacer 36 a second distance in the caudal direction. In one example, the second distance can be greater than the first distance. Alternatively, the second distance can be substantially equal to or less than the first distance.

The plate 34 can define a first or dorsal plate end 54 and a second or ventral plate end 56 that is disposed opposite the dorsal plate end 54. The ventral plate end 56 can face away from the spacer 36. The dorsal plate end 54 is opposite the ventral plate end 56 in the dorsal direction. It should be appreciated that the anatomical terms "cranial," "caudal," dorsal," "ventral," and other anatomical directional terms as applied to the implant 20 can apply to the respective anatomical directions when the implant 20 is implanted. The anatomical terms can equally apply to the implant 20 when disposed outside the body as relative directional terms. A cranial portion 55 of the dorsal plate end 54 can extend out with respect to the cranial surface 42 of the spacer 36 in the cranial direction. A caudal portion 57 of the dorsal plate end 54 can extend out with respect to the caudal surface 44 of the spacer 36 in the caudal direction. The caudal portion 57 of the dorsal plate end 54 can extend out with respect to the caudal surface 44 of the spacer 36 a distance that is greater than the distance at which the cranial portion 55 of the dorsal plate end 54 extends out with respect to the cranial surface 42 of the spacer 36.

Figure 5A:
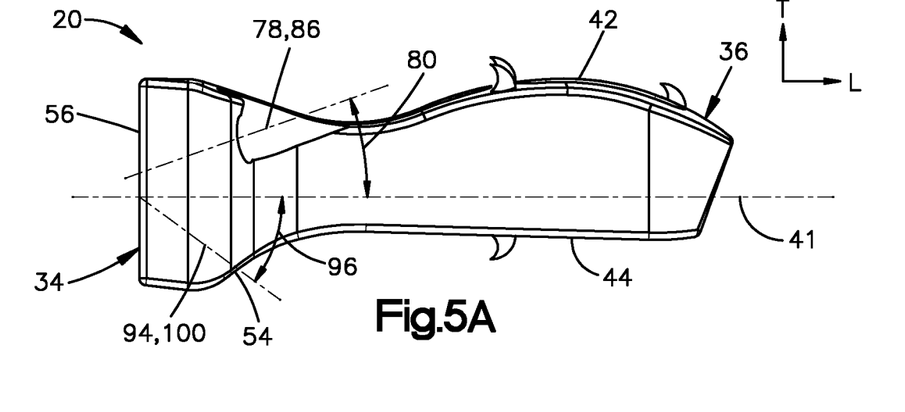
FIG. 5A is a side elevation view of the intervertebral implant illustrated in FIG. 2A, showing a trajectory of cranial fixation apertures and caudal fixation apertures that extend through the plate.

Further, as shown in FIG. 5A, the cranial portion 55 of the dorsal plate end 54 and the cranial surface 42 of the spacer 36 can define a concavity 59 in the first plane at a cranial interface between the spacer 36 and the plate 34. Thus, the implant 20 can include a cranial implant surface that is configured to be inserted into the intervertebral space and nest with anatomical geometry of the cranial vertebral body 30. The cranial implant surface can include the cranial surface 42 and the cranial interface. Accordingly, the cranial implant surface, which can be defined by the cranial surface 42 of the spacer 36 and the cranial portion 55 of the dorsal plate end 54, can define a concavo-convex geometry in the first plane that is oriented along the transverse direction T and the longitudinal direction L. The concavo-convex geometry can include the concavity defined at the interface between the cranial portion 55 of the dorsal plate end 54 and the cranial surface 42 of the spacer 36. The convex portion of the concavo-convex geometry can be defined by the convex cranial surface 42 of the spacer 36.

The caudal portion 57 of the dorsal plate end 54 and the caudal surface 44 of the spacer 36 can combine to define a caudal concavity 61 at a caudal interface between the spacer 36 and the plate 34 in the first plane. Thus, the implant 20 can define a caudal implant surface that is configured to be inserted into the intervertebral space and nest with anatomical geometry of the caudal vertebral body 30. The caudal implant surface of the implant can include the caudal surface 44 of the spacer 36 and the caudal interface between the spacer 36 and the plate 34. At least a portion of the caudal concavity 61 can be offset from the cranial concavity 59 in the ventral direction. Further, the caudal concavity 61 can have a greater curvature than the cranial concavity 59. As shown in FIG. 1A, the cranial portion 55 of the dorsal plate end 54 can face or abut the cranial vertebral body 28, and the caudal portion 57 of the dorsal plate end 54 can face or abut the caudal vertebral body 30.

Referring now to FIGS. 3-5C, the implant 20 can include at least one fixation aperture 63 such as a plurality of fixation apertures that extend through the plate 34. In particular, the at least one fixation aperture 63 can extend from the ventral plate end 56 to the dorsal plate end 54. The at least one fixation aperture 63 extends from the ventral plate end 56 to the dorsal plate end 54 along a central aperture axis. An intervertebral implant system can include the implant 20 and at least one bone fixation element 58 that is configured to be inserted through the at least one fixation aperture, respectively, and driven into an aligned one of the cranial and caudal vertebral bodies, thereby fixing the implant 20 to the respective vertebral body. The bone fixation element 58 can be configured as a bone screw 60 having a head 62 and a shaft 64 that extends out with respect to the head 62 and is configured to purchase with bone. The shaft 64 can include at least one thread 66 that is configured to threadedly purchase with bone. Thus, as the bone screw 60 is driven into the vertebral body, the threaded shaft 64 threadedly purchases with the vertebral body.

The at least one bone screw 60 can be configured as a locking screw that is configured to threadedly purchase with the implant in the respective at least one fixation aperture 63. Thus, the head 62 can carry at least one thread 68, and the implant 20 can carry at least one thread 70 in the at least one fixation aperture 63. The thread of the bone screw head 62 can thus threadedly mate with the thread of the implant 20 as the bone screw 60 is driven into the vertebra.

Alternatively, the at least one bone screw 60 can be configured as a compression screw that applies a compressive force to the implant 20 against the vertebral body as the bone screw is driven into the vertebral body. The head 62 of the bone screw 60 can be thus unthreaded, and thus configured to apply a compressive force against the plate 34 in the respective at least one fixation aperture 63 as the shaft 64 is driven into the vertebral body. Thus, the at least one fixation aperture 63 can similarly be unthreaded, and receive the force from the head 62, which in turn causes the implant 20 to compress toward or against the respective vertebral body.

In one example, the at least one fixation aperture 63 can include at least one cranial fixation aperture that extends along a cranial aperture axis. In particular, the at least one fixation aperture 63 can include a pair of cranial fixation apertures, including a first cranial fixation aperture 72 and a second cranial fixation aperture 74. The first cranial fixation aperture 72 can define a first or dorsal opening 76a in the dorsal plate end 54 of the plate 34, and a second or ventral opening 76b in the ventral plate end 56 of the plate 34. The first cranial fixation aperture 72 can extend along a first cranial aperture axis 78. The first cranial aperture axis 78 can thus extend centrally through each of the dorsal opening 76a and the ventral opening 76b. The first cranial aperture axis 78 can be straight and linear.

Referring now also to FIG. 5A, the first cranial fixation aperture 72 can be oriented along a trajectory that flares outward in the cranial direction as the first cranial fixation aperture 72 extends in the dorsal direction. Thus, the first cranial aperture axis 78 can flare outward in the cranial direction as the first cranial aperture axis 78 extends in the dorsal direction. It should therefore be appreciated that the center of the dorsal opening 76a can be offset in the cranial direction with respect to the central of the ventral opening 76b. It should be appreciated that the first cranial aperture axis 78 can define a cranial angle 80 with respect to a reference plane 41 that is oriented along the lateral direction A and the longitudinal direction L with respect to a view from the lateral direction A of the first cranial aperture axis 78 and the reference plane 41. The angle 80 thus defines the extent that the first cranial aperture axis 78 flares in the cranial direction as it extends in the dorsal direction. The angle 80 can be any suitable angle as desired. In one example, the angle 80 can range from approximately 5 degrees to approximately 45 degrees. For instance the angle 80 can range from approximately 10 degrees to approximately 30 degrees. In one example, the angle 80 can range from approximately 15 degrees to approximately 25 degrees. For instance, the angle can be approximately 20 degrees.

Additionally, the first cranial aperture axis 78 can be spaced in the cranial direction from the cranial surface 42 of the spacer 36 both as the axis 78 exits the plate 34 and as the first cranial aperture axis 78 extends in the dorsal direction from the plate 34. Further, an entirety of the first dorsal opening 76a can be offset from the cranial surface 42 of the spacer 36 in the cranial direction. Thus, when the bone screw 60 is inserted through the first cranial fixation aperture 72 an entirety of the bone screw shaft 62 that extends out from the first cranial fixation aperture 72 in the dorsal direction can be spaced from the cranial surface 42 of the spacer 36 in the cranial direction. Further, because the bone screw shaft 62 extends along the first cranial aperture axis 78, the bone screw shaft 62 extends outward in the cranial direction as it extends in the dorsal direction.

Figure 5B:
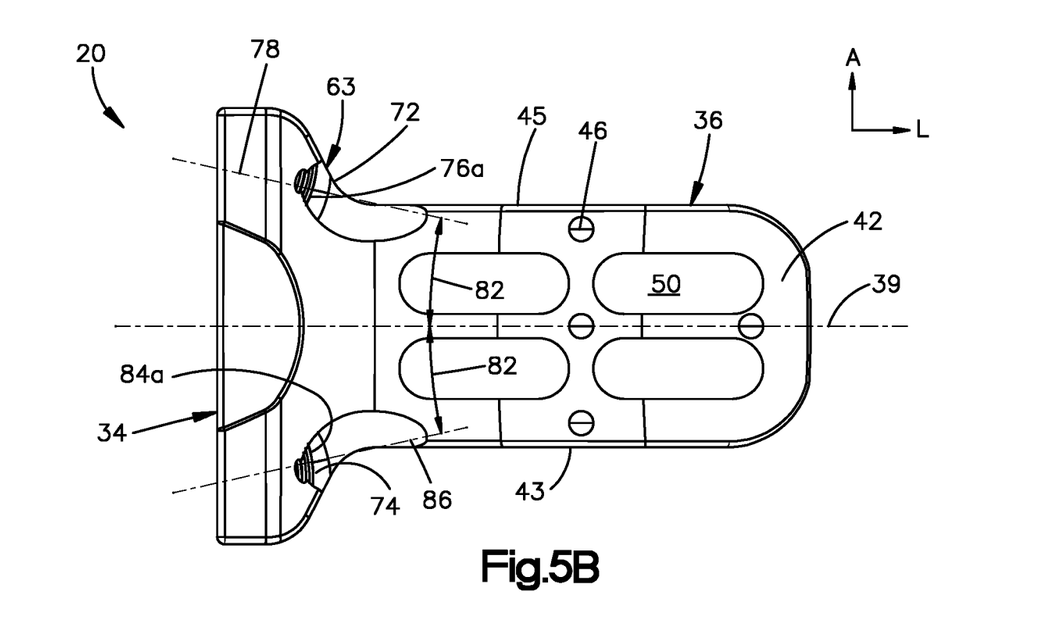
FIG. 5B is a cranial plan view of the intervertebral implant illustrated in FIG. 2A, showing a lateral trajectory of cranial fixation apertures that extend through the plate.
Figure 5C:
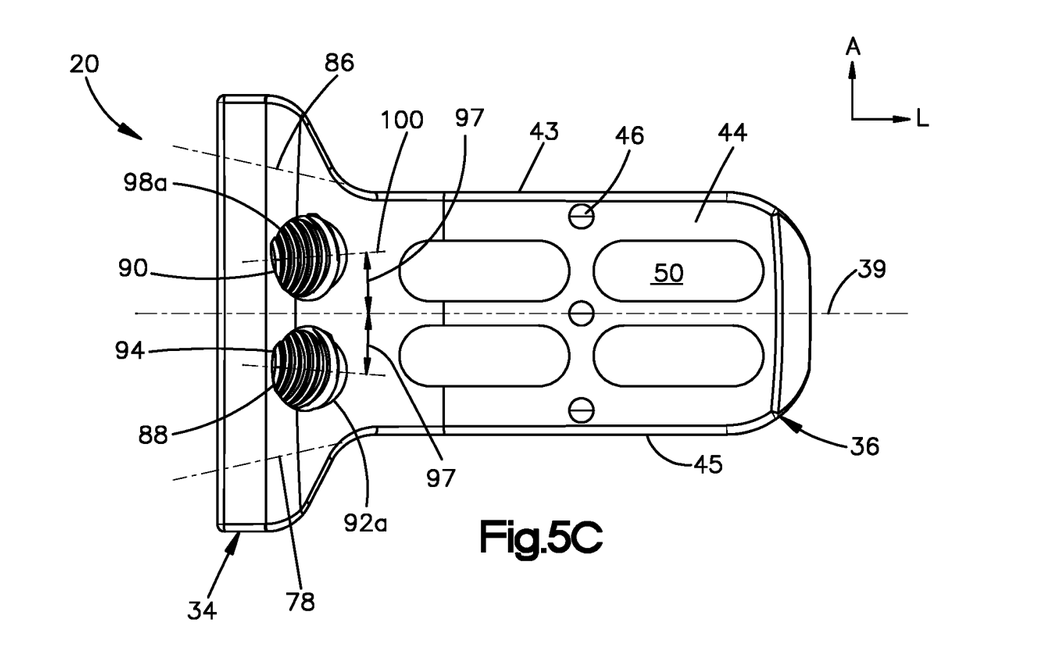
FIG. 5C is a caudal plan view of the intervertebral implant illustrated in FIG. 2A, showing a lateral trajectory of caudal fixation apertures that extend through the plate.
Figure 6A:
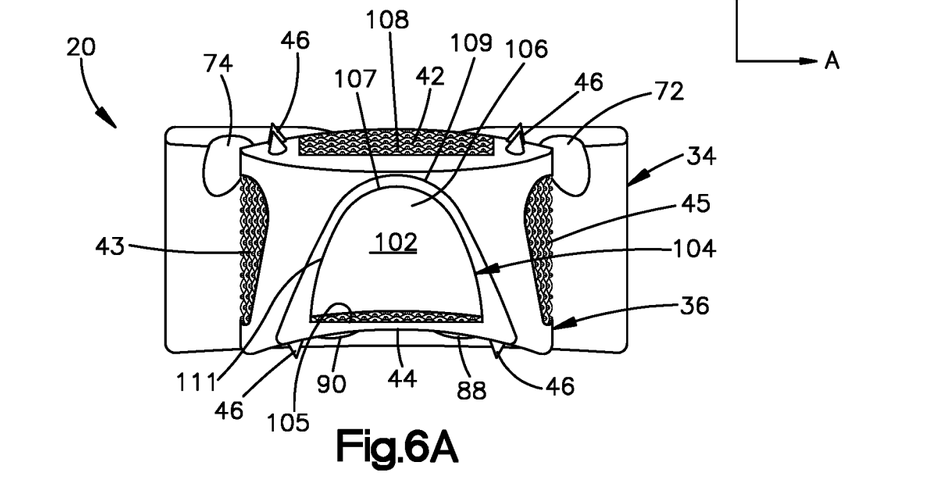
FIG. 6A is an end view of the intervertebral implant illustrated in FIG. 2A, but including a bone graft retention cavity in accordance with another embodiment.
Figure 6B:
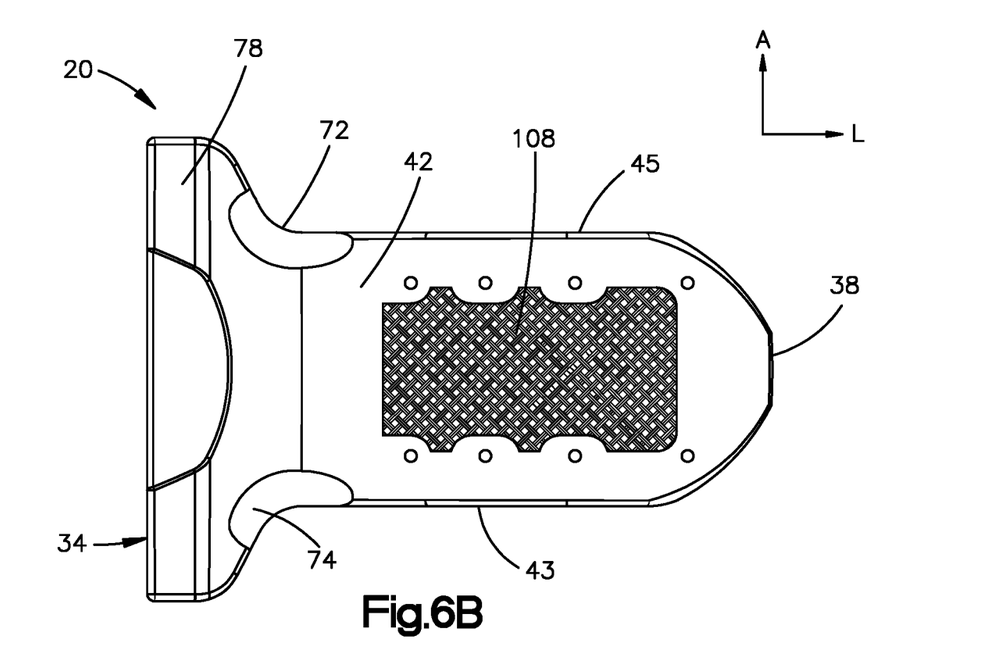
FIG. 6B is a cranial plan view of the intervertebral implant illustrated in FIG. 6A.
Figure 6C:
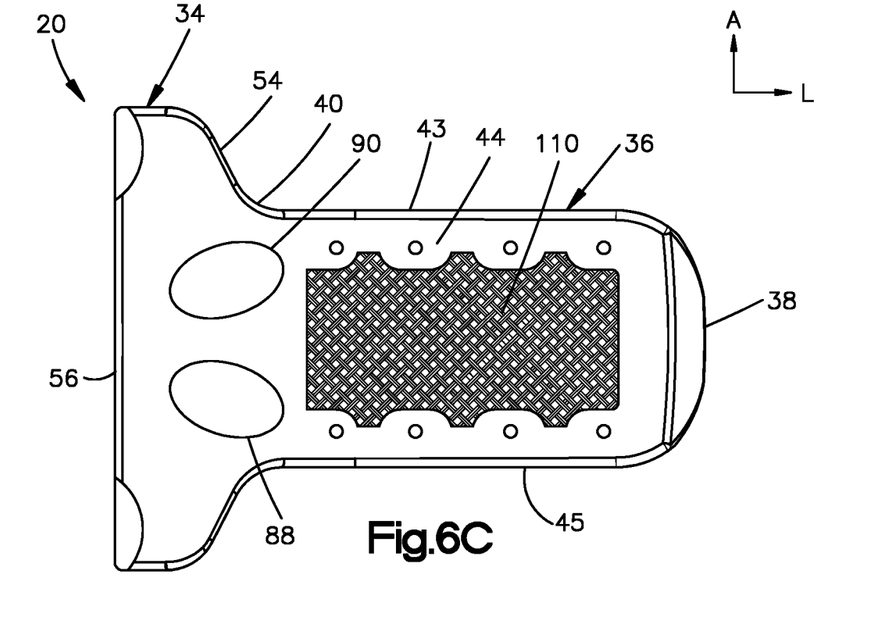
FIG. 6C is a caudal plan view of the intervertebral implant illustrated in FIG. 6A.
Figure 6D:
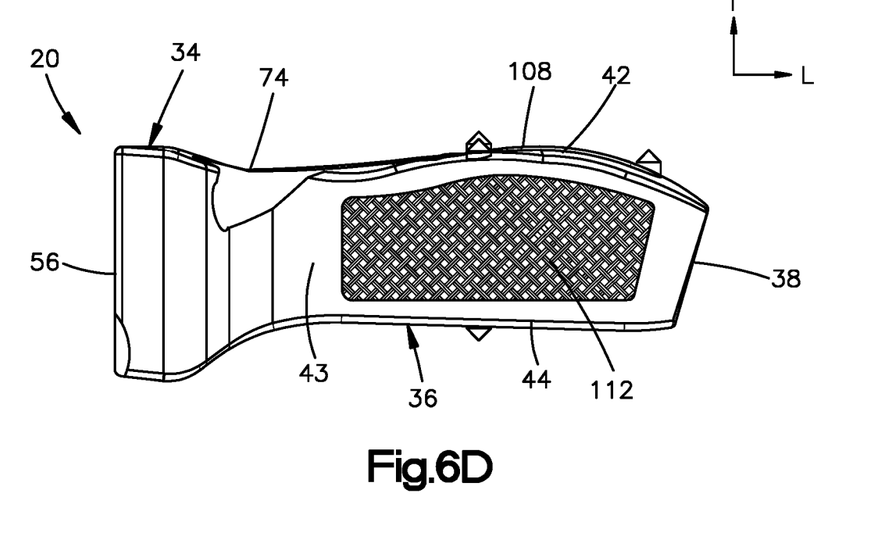
FIG. 6D is a side elevation view of the intervertebral implant illustrated in FIG. 6A.

Referring to FIGS. 5B-5C, the first cranial aperture axis 78 can further flare laterally inward (or medially) toward the midplane of the spacer 36 as the axis 78 extends in the dorsal direction through the plate 34. Thus, the center of the dorsal opening 76a can be spaced a first distance from the midplane 39 along the lateral direction A, and the center of the ventral opening 76b can be spaced a second distance from the midplane 39 along the lateral direction that is greater than the first distance. The first cranial aperture axis 78 and the midplane 39 can define a cranial lateral angle 82 that can be any suitable angle as desired. In one example, the angle 82 can range from approximately 5 degrees to approximately 25 degrees. For instance, the angle 82 can range from approximately 10 degrees to approximately 15 degrees. In one particular example, the angle 82 can be approximately 12 degrees. The first cranial aperture axis 78 can intersect the midplane 39 at a location that is spaced in the dorsal direction from the leading end 38 of the spacer 36, and thus outside the footprint of the spacer 20.

The second cranial fixation aperture 74 can define a first or dorsal opening 84a in the dorsal plate end 54 of the plate 34, and a second or ventral opening 84b in the ventral plate end 56 of the plate 34. The second cranial fixation aperture 74 can extend along a second cranial aperture axis 86. The second cranial aperture axis 86 can thus extend centrally through each of the dorsal opening 84a and the ventral opening 84b. The second cranial aperture axis 86 can be straight and linear.

As illustrated in FIG. 5A, the second cranial fixation aperture 74 can be oriented along a trajectory that flares outward in the cranial direction as the second cranial fixation aperture 74 extends in the dorsal direction. Thus, the second cranial aperture axis 86 can flare outward in the cranial direction as the second cranial aperture axis 86 extends in the dorsal direction. It should therefore be appreciated that the center of the dorsal opening 84a can be offset in the cranial direction with respect to the central of the ventral opening 84b. It should be appreciated that the second cranial aperture axis 86 can define the cranial angle 82 with respect to the reference plane 41 that is oriented along the lateral direction A and the longitudinal direction L with respect to a view from the lateral direction A of the first cranial aperture axis 86 and the reference plane 41.

Additionally, the second cranial aperture axis 86 can be spaced in the cranial direction from the cranial surface 42 of the spacer 36 both as the axis 86 exits the plate 34 and as the axis 78 extends in the dorsal direction from the plate 34. Further, an entirety of the dorsal opening 84a can be offset from the cranial surface 42 of the spacer 36 in the cranial direction. Thus, when the bone screw 60 is inserted through the second cranial fixation aperture 74, an entirety of the bone screw shaft 62 that extends out from the second cranial fixation aperture 74 in the dorsal direction can be spaced from the cranial surface 42 of the spacer 36 in the cranial direction. Further, because the bone screw shaft 62 extends along the second cranial aperture axis 86, the bone screw shaft 62 extends outward in the cranial direction as it extends in the dorsal direction.

Referring to FIG. 5B, the second cranial aperture axis 86 can further flare laterally inward (or medially) toward the midplane 39 of the spacer 36 as the axis 86 extends in the dorsal direction through the plate 34. Thus, the center of the dorsal opening 84a can be spaced the first distance from the midplane 39 along the lateral direction A, and the center of the ventral opening 84b can be spaced the second distance from the midplane 39 along the lateral direction that is greater than the first distance. The second cranial aperture axis 86 and the midplane 39 can define the lateral angle 82 described above. The second cranial aperture axis 86 can intersect the midplane 39 at a location that is spaced in the dorsal direction from the leading end 38 of the spacer 36, and thus outside the footprint of the implant 20.

The first and second cranial fixation apertures 72 can be spaced substantially equidistantly from the midplane 39, and positioned at opposed sides of the midplane 39. Further, the first and second cranial aperture axes 78 and 86 can converge toward each other at an angle which can be approximately twice the lateral angle 82. Further still, the lateral angle 82 can be less than the cranial angle 80. Further still, the first and second cranial aperture axes 78 and 86 can flare outward in the cranial direction at the same angle as they extend in the dorsal direction.

Referring now to FIGS. 5A-5C, the at least one fixation aperture 63 can include at least one caudal fixation aperture that extends along a caudal aperture axis. In particular, the at least one fixation aperture 63 can include a pair of caudal fixation apertures, including a first caudal fixation aperture 88 and a second caudal fixation aperture 90. The first and second caudal fixation apertures 88 and 90 can be offset laterally inward (or medially) with respect to the first and second cranial fixation apertures 72 and 74. The first caudal fixation aperture 88 can define a first or dorsal opening 92a in the dorsal plate end 54 of the plate 34, and a second or ventral opening 92b in the ventral plate end 56 of the plate 34. The first caudal fixation aperture 88 can extend along a first caudal aperture axis 94. The first caudal aperture axis 94 can thus extend centrally through each of the dorsal opening 92a and the ventral opening 92b. The first caudal aperture axis 94 can be straight and linear.

Referring to FIG. 5A, the first caudal fixation aperture 88 can be oriented along a trajectory that flares outward in the caudal direction as the first caudal fixation aperture 88 extends in the dorsal direction. Thus, the first caudal aperture axis 94 can flare outward in the caudal direction as the first caudal aperture axis 94 extends in the dorsal direction. It should therefore be appreciated that the center of the dorsal opening 92a can be offset in the caudal direction with respect to the central of the ventral opening 92b. It should further be appreciated that the first caudal aperture axis 94 can define a caudal angle 96 with respect to the reference plane 41 that is oriented along the lateral direction A and the longitudinal direction L with respect to a view from the lateral direction A of the first caudal aperture axis 94 and the reference plane 41. The angle 96 thus defines the extent that the first caudal aperture axis 94 flares in the caudal direction as it extends in the dorsal direction. The angle 96 can be any suitable angle as desired. In one example, the angle 96 can range from approximately 10 degrees to approximately 60 degrees. For instance the angle 96 can range from approximately 20 degrees to approximately 55 degrees. In one example, the angle 96 can range from approximately 30 degrees to approximately 50 degrees. For instance, the angle can be approximately 40 degrees. Thus, the caudal angle 96 can be greater than the cranial angle 80. For instance, the caudal angle 96 can be approximately double the cranial angle 80.

Additionally, the first caudal aperture axis 94 can be spaced in the caudal direction from the caudal surface 44 of the spacer 36 both as the axis 94 exits the plate 34 and as the axis 94 extends in the dorsal direction from the plate 34. Further, an entirety of the first dorsal opening 92a can be offset from the caudal surface 44 of the spacer 36 in the caudal direction. Thus, when the bone screw 60 is inserted through the first caudal fixation aperture 88 an entirety of the bone screw shaft 62 that extends out from the first caudal fixation aperture 88 in the dorsal direction can be spaced from the caudal surface 44 of the spacer 36 in the caudal direction. Further, because the bone screw shaft 62 extends along the first caudal aperture axis 94, the bone screw shaft 62 extends outward in the caudal direction as it extends in the dorsal direction.

Referring now to FIG. 5C, the first caudal aperture axis 94 can further flare laterally outward away from the midplane of the spacer 36 as the axis 94 extends in the dorsal direction through the plate 34. Otherwise stated, the first caudal aperture axis 94 can flare laterally inward toward the midplane of the spacer 36 as the axis 94 extends in the ventral direction. Further, the center of the dorsal opening 92a can be spaced a first distance from the midplane 39 along the lateral direction A, and the center of the ventral opening 92b can be spaced a second distance from the midplane 39 along the lateral direction that is less than the first distance. The first caudal aperture axis 94 and the midplane 39 can define a caudal lateral angle 97 that can be any suitable angle as desired. In one example, the angle 97 can range from approximately 2 degrees to approximately 20 degrees. For instance, the angle 97 can range from approximately 2 degrees to approximately 10 degrees. In one particular example, the angle 97 can be approximately 5 degrees. The first caudal aperture axis 94 can intersect the midplane 39 at a location that is spaced in the ventral direction from the ventral plate end 56 of the plate 34, and thus outside the footprint of the implant 20. Alternatively, the first caudal aperture axis 94 can extend in the dorsal direction substantially parallel to the midplane 39.

The second caudal fixation aperture 90 can define a first or dorsal opening 98a in the dorsal plate end 54 of the plate 34, and a second or ventral opening 98b in the ventral plate end 56 of the plate 34. The first and second caudal fixation apertures 88 and 90 extend through the plate 34 a distance from the respective dorsal opening to the respective ventral opening that is less than the distance that the cranial fixation apertures 72 and 74 extend from the respective dorsal opening to the respective ventral opening. The second caudal fixation aperture 90 can extend along a second caudal aperture axis 100. The second caudal aperture axis 100 can thus extend centrally through each of the dorsal opening 98a and the ventral opening 98b. The second caudal aperture axis 100 can be straight and linear.

As illustrated in FIG. 5A, the second caudal fixation aperture 90 can be oriented along a trajectory that flares outward in the caudal direction as the second caudal fixation aperture 90 extends in the dorsal direction. Thus, the second caudal aperture axis 100 can flare outward in the caudal direction as the second caudal aperture axis 100 extends in the dorsal direction. It should therefore be appreciated that the center of the dorsal opening 98a can be offset in the caudal direction with respect to the central of the ventral opening 98b. It should further be appreciated that the second caudal aperture axis 100 can define the caudal angle 96 described above with respect to the reference plane 41 with respect to a view from the lateral direction A of the second caudal aperture axis 100 and the reference plane 41.

Additionally, the second caudal aperture axis 100 can be spaced in the caudal direction from the caudal surface 44 of the spacer 36 both as the axis 100 exits the plate 34 and as the axis 100 extends in the dorsal direction from the plate 34. Further, an entirety of the first dorsal opening 98a can be offset from the caudal surface 44 of the spacer 36 in the caudal direction. Thus, when the bone screw 60 is inserted through the second caudal fixation aperture 90, an entirety of the bone screw shaft 62 that extends out from the first caudal fixation aperture 90 in the dorsal direction can be spaced from the caudal surface 44 of the spacer 36 in the caudal direction. Further, because the bone screw shaft 62 extends along the second caudal aperture axis 100, the bone screw shaft 62 extends outward in the caudal direction as it extends in the dorsal direction.

Referring to FIG. 5C, the second caudal aperture axis 100 can further flare laterally outward away from the midplane 39 of the spacer 36 as the axis 94 extends in the dorsal direction through the plate 34. Otherwise stated, the second caudal aperture axis 100 can flare laterally inward toward the midplane 39 of the spacer 36 as the axis 100 extends in the ventral direction. Thus, the first and second caudal aperture axes 94 and 100, respectively, can be sloped opposite the first and second cranial aperture axes 78 and 86, respectively. Thus, the center of the dorsal opening 98a can be spaced a first distance from the midplane 39 along the lateral direction A, and the center of the ventral opening 98b can be spaced a second distance from the midplane 39 along the lateral direction that is less than the first distance. The second caudal aperture axis 100 and the midplane 39 can define the lateral angle 97 described above. Thus, the second caudal aperture axis 100 can intersect the midplane 39 at a location that is spaced in the ventral direction from the ventral plate end 56 of the plate 34, and thus outside the footprint of the implant 20. Alternatively, the second caudal aperture axis 100 can extend in the dorsal direction substantially parallel to the midplane 39.

The first and second caudal fixation apertures 88 and 90 can be spaced substantially equidistantly from the midplane 39, and positioned at opposed sides of the midplane 39. Further, as the first and second caudal aperture axes 94 and 100 extend along the dorsal direction, the axes 94 and 100 can diverge away from each other at an angle which can be approximately twice the lateral angle 97. Further still, the lateral angle 97 can be less than the caudal angle 96. Further still, the first and second caudal aperture axes 94 and 100 can flare outward in the caudal direction at the same angle as they extend in the dorsal direction.

While the plate 34 has been described as including the first and second cranial fixation apertures 72 and 74 and the first and second caudal fixation apertures 88 and 90, it will be appreciated that the plate 34 can include any one or more fixation apertures configured to receive the bone fixation elements 58 such as, for example, one or more bone screws 60, respectively, for securing the intervertebral implant 20 to the adjacent vertebral bodies 28 and 30. The plate 34 may include any number of fixation apertures arranged in any number of combinations. For example, the plate 34 may include two, three, four or more fixation apertures for receiving, preferably, an equal number of bone screws 60. Moreover, the fixation apertures can alternatively repeatedly alternate with one another, whereby one fixation aperture is angled cranially so as to define a cranial fixation aperture, and an adjacent fixation aperture is angled caudally so as to define a caudal fixation aperture. Thus, a cranial fixation aperture can be surrounded on both lateral sides by a caudal fixation aperture. Further, a caudal fixation aperture can be surrounded on both lateral sides by a cranial fixation aperture.

Referring again to FIG. 2A, the intervertebral implant 20 can have any suitable dimensions as desired. For instance, the spacer 36 can have a spacer length along the longitudinal direction L from the leading end 38 to the trailing end 40 that is in the range from approximately 12 mm to approximately 24 mm. The spacer 36 can have a spacer width along the lateral direction from the first lateral wall 43 to the second lateral wall 45 that is in the range from approximately 4 mm to approximately 20 mm. For instance, the spacer width can range from approximately 10 mm to approximately 16 mm. The plate 34 can have a plate length along the longitudinal direction L from the dorsal end 54 to the ventral end 56 that is in the range from approximately 3 mm to approximately 10 mm. In one example, the plate length can be approximately 6.5 mm.

During operation, and referring generally to FIGS. 1A-5C, the plate 34 can be inserted into the intervertebral disc space 32 between the adjacent vertebral bodies 28 and 30, such that the cranial portion 55 of the dorsal plate end 54 of the plate 34 faces the cranial vertebral body 28 and the caudal portion 57 of the dorsal plate end faces the caudal vertebral body 30. In one example, the cranial portion 55 of the dorsal plate end 54 of the plate 34 can abut the cranial vertebral body 28, and the caudal portion 57 of the dorsal plate end can abut the caudal vertebral body 30. The concavo-convex geometry of the cranial surface of the implant 20 can geometrically nest with an anatomical geometry of the cranial vertebral body 28. The caudal surface of the implant 20 can geometrically nest with the anatomical geometry of the cranial vertebral body 28.

Next, a plurality of bone screws 60 can be inserted through respective ones of the cranial and caudal fixation apertures 78, 80, 88, and 90, respectively. The bone screws 60 inserted into the cranial fixation apertures 72 and 74 can be driven into the cranial vertebral body 28. The respective trajectories of the first and second cranial aperture axes 78 and 86 can cause the bone screws 60 to purchase in dense cortical bone of the cranial vertebral body 28. Thus, a reliable fixation to the cranial vertebral body 28 can be achieved. Similarly, the bone screws 60 inserted into the caudal fixation apertures 88 and 90 can be driven into the caudal vertebral body 30. The respective trajectories of the first and second caudal aperture axes 94 and 100 can cause the bone screws 60 to purchase in dense cortical bone of the caudal vertebral body 30. Thus, a reliable fixation to the cranial vertebral body 30 can be achieved.

Referring now to FIGS. 6A-6D, the intervertebral implant 20 can be constructed as described above, but as an alternative to the windows 50 and ribs 51 and 53, the implant 20 can include a bone graft cavity 102 that is configured to receive bone graft material that can further fuse the intervertebral implant 20 to the first and second vertebral bodies 28 and 30. In particular, the bone graft cavity 102 can have a first open end 104 that is configured to receive bone graft material, such as allograft, autograft, or the like. The open end 104 can extend through the leading end 38 of the spacer 36 along the longitudinal direction L in one example. It is appreciated that the open end 104 is not limited to the leading end of the spacer 36. For instance, the open end 104 can alternatively extend through one of the first and second lateral walls 43 and 45, respectively.

In one example, the bone graft cavity 102 can extend in the rearward direction from the open end 104 to a wall 106 that defines a closed end of the bone graft cavity 102. The wall 106 can be defined by the spacer 36, or can alternatively be defined by the plate 34. The cavity 102 can also be partially defined by one or more up to all of the cranial wall, the caudal wall, and one or both of the first and second lateral walls. For instance, the cranial wall can include a cranial lattice structure 108 that defines a cranial end of the bone graft cavity 102. In this regard, it should be appreciated that the spacer 36 defines a plurality of openings that extend through the cranial wall and are open to the bone graft cavity 102. The openings can be defined by the cranial lattice structure 108, or can be otherwise defined as desired. The caudal wall can include a caudal lattice structure 110 that defines a caudal end of the bone graft cavity 102. In this regard, it should be appreciated that the spacer 36 defines a plurality of openings that extend through the caudal wall and are open to the bone graft cavity 102. The openings can be defined by the caudal lattice structure 110, or can be otherwise defined as desired. The cranial lattice structure 108 and the caudal lattice structure 110 can be spaced from each other along the transverse direction T.

The first lateral wall can include a first and second lateral lattice structures 112 that define the first and second lateral ends of the bone graft cavity 102, respectively. Thus, the first and second lateral lattice structures 112 can be spaced from each other along the lateral direction A. In this regard, it should be appreciated that the spacer 36 defines a plurality of openings that extend through the first and second lateral walls and are open to the bone graft cavity 102. The openings can be defined by the lateral lattice structures 112, or can be otherwise defined as desired.

During operation, bone graft material can be inserted through the open end 104 and into the bone graft cavity 102. The bone graft material can thus extend through one or more up to all of the openings in the cranial, caudal, and lateral walls. Thus, the bone graft material can extend through openings in the cranial lattice structure 108 and can contact the cranial vertebral body. Similarly, the bone graft material can extend through openings in the caudal lattice structure 110 and can contact the caudal vertebral body. Further still, the bone graft material can extend through openings in the first and second lateral lattice structures 112, and can fuse with bony ingrowth that grows around the intervertebral implant 20.

The open end 104 can define any suitable shape as desired. For instance, the open end 104 can be defined by a substantially planar caudal surface 105, and a concave surface 107 that adjoins opposed ends of the planar caudal surface. The concave surface 107 can include a cranial substantially arc-shaped surface 109 and a pair of laterally opposed segments 111 that flare away from each other as they extend from opposed ends of the substantially arc-shaped surface 109 to opposed ends of the caudal surface 105. The concave surface 107 can be defined by a single curved surface, or by a plurality of surfaces that can include one or more of curved segments, and straight segments that are angled with respect to each other. The open end 104 can further be defined by a beveled lead-in surface. It should be appreciated, of course, that the open end 104 can have any suitable geometry as desired.

It should be understood that the foregoing description is only illustrative of the present invention. Various alternatives and modifications can be devised by those skilled in the art without departing from the present invention. Accordingly, the present invention is intended to embrace all such alternatives, modifications, and variances that fall within the scope of the appended claims.

What is claimed is:

1. An intervertebral implant configured to be implanted in an intervertebral disc space of a quadruped, the intervertebral disc space defined by a cranial vertebral body and a caudal vertebral body, the implant comprising:
   a plate defining a ventral plate end and a dorsal plate end spaced opposite the ventral plate end in a dorsal direction, and a plurality of fixation apertures that extend through the plate from the ventral plate end to the dorsal plate end; and
   a spacer that extends in the dorsal direction from the plate, wherein the spacer defines a caudal surface that is configured to face and abut the caudal vertebral body, and a cranial surface that is opposite the caudal surface in a cranial direction and is configured to face and abut the cranial vertebral body, the caudal and cranial surfaces configured to grip the caudal and cranial vertebral bodies, respectively,
   wherein the cranial surface is convex in a first plane that is oriented along the dorsal direction and the cranial direction, and the cranial surface is convex in a second plane that is oriented along the cranial direction and a lateral direction that is substantially perpendicular to each of the dorsal direction and the cranial direction,
   wherein the caudal surface is substantially straight and linear in the first plane, and the caudal surface is concave in the second plane, and
   wherein the cranial surface defines a first radius of curvature in the first plane, and a second radius of curvature in the second plane that is greater than the first radius of curvature.

2. The intervertebral implant as recited in claim 1, wherein the first radius of curvature ranges from approximately 5 mm to approximately 20 mm.

3. The intervertebral implant as recited in claim 1, wherein the second radius of curvature ranges from approximately 10 mm to approximately 25 mm.

4. The intervertebral implant as recited in claim 1, further comprising a plurality of teeth that project out from the cranial and caudal surfaces, wherein each tooth of the plurality of teeth defines leading and trailing surfaces having respective distal ends that extend in a ventral direction as they converge to a tip, the ventral direction opposite the dorsal direction.

5. The intervertebral implant as recited in claim 1, further comprising a bone graft cavity configured to receive bone graft material to fuse the implant to the cranial and caudal vertebral bodies.

6. The intervertebral implant as recited in claim 5, wherein the bone graft cavity has an opening at a leading end of the spacer.

7. The intervertebral implant as recited in claim 1, further comprising a plurality of windows configured to receive bone graft material, wherein the windows extend through the spacer from the cranial surface to the caudal surface.

8. The intervertebral implant as recited in claim 1, wherein the plate and spacer are monolithic with each other.

9. The intervertebral implant as recited in claim 1, wherein the dorsal plate end comprises a cranial portion that extends out with respect to the cranial surface of the spacer in the cranial direction, and the dorsal plate end further comprises a caudal portion that extends out with respect to the caudal surface of the spacer in the caudal direction.

10. The intervertebral implant as recited in claim 1, wherein the plurality of fixation apertures comprises a first cranial aperture that extends through the plate along a first cranial aperture axis that flares in the cranial direction as it extends in the dorsal direction, and a first caudal aperture that extends through the plate along a first caudal aperture axis that flares in the caudal direction as it extends in the dorsal direction.

11. The intervertebral implant as recited in claim 10, wherein the first cranial aperture axis defines a cranial angle with respect to a reference plane that is oriented along the lateral direction A and the dorsal direction, and the first caudal aperture axis defines a caudal angle with respect to the reference plane that is greater than the cranial angle.

12. The intervertebral implant as recited in claim 11, wherein the cranial angle ranges from approximately 10 degrees to approximately 30 degrees, and the caudal angle ranges from approximately 30 degrees to approximately 50 degrees.

13. The intervertebral implant as recited in claim 10, wherein the first cranial aperture axis is angled toward a midplane as it extends in the dorsal direction, and the first caudal aperture axis is angled toward the midplane as it extends in a ventral direction that is opposite the dorsal direction, wherein the midplane is oriented along the cranial direction and the dorsal direction.

14. The intervertebral implant as recited in claim 13, wherein the first cranial aperture axis and the midplane define a cranial lateral angle that ranges from approximately 5 degrees to approximately 25 degrees.

15. The intervertebral implant as recited in claim 13, wherein the first caudal aperture axis and the midplane define a caudal lateral angle that ranges from approximately 2 degrees to approximately 10 degrees.

16. The intervertebral implant as recited in claim 13, comprising first and second cranial apertures, and first and second caudal apertures that are disposed between the cranial apertures with respect to the lateral direction.

17. An intervertebral implant system comprising the intervertebral implant recited in claim 16, and a plurality of screws configured to be inserted through respective ones of the cranial apertures and the caudal apertures, driven into the cranial vertebral body and the caudal vertebral body, respectively.

18. An intervertebral implant configured to be implanted in an intervertebral disc space of a quadruped, the intervertebral disc space defined by a cranial vertebral body and a caudal vertebral body, the implant comprising:

a plate defining a ventral plate end and a dorsal plate end spaced opposite the ventral plate end in a dorsal direction, and a plurality of fixation apertures that extend through the plate from the ventral plate end to the dorsal plate end; and a spacer that extends in the dorsal direction from the plate, wherein the spacer defines a caudal surface that is configured to face and abut the caudal vertebral body, and a cranial surface that is opposite the caudal surface in a cranial direction and is configured to face and abut the cranial vertebral body, the caudal and cranial surfaces configured to grip the caudal and cranial vertebral bodies, respectively, wherein the cranial surface is convex in a first plane that is oriented along the dorsal direction and the cranial direction, and the cranial surface is convex in a second plane that is oriented along the cranial direction and a lateral direction that is substantially perpendicular to each of the dorsal direction and the cranial direction, wherein the caudal surface is substantially straight and linear in the first plane, and the caudal surface is concave in the second plane, and wherein the implant defines a cranial implant surface that is defined by the cranial surface of the spacer and the cranial portion of the dorsal plate end, and the cranial implant surface has a concavo-convex geometry in the first plane.

19. An intervertebral implant configured to be implanted in an intervertebral disc space of a quadruped, the intervertebral disc space defined by a cranial vertebral body and a caudal vertebral body, the implant comprising;

a plate defining a ventral plate end and a dorsal plate end spaced opposite the ventral plate end in a dorsal direction, and a plurality of fixation apertures that extend through the plate from the ventral plate end to the dorsal plate end; and a spacer that extends in the dorsal direction from the plate, wherein the spacer defines a caudal surface that is configured to face and abut the caudal vertebral body, and a cranial surface that is opposite the caudal surface in a cranial direction and is configured to face and abut the cranial vertebral body, the caudal and cranial surfaces configured to grip the caudal and cranial vertebral bodies, respectively, wherein the cranial surface is convex in a first plane that is oriented along the dorsal direction and the cranial direction, and the cranial surface is convex in a second plane that is oriented along the cranial direction and a lateral direction that is substantially perpendicular to each of the dorsal direction and the cranial direction, wherein the caudal surface is substantially straight and linear in the first plane, and the caudal surface is concave in the second plane, and wherein the implant defines a caudal concavity in the first plane at a caudal interface between the spacer and the plate.

* * * * *